US009603671B2

(12) United States Patent
Hladio et al.

(10) Patent No.: US 9,603,671 B2
(45) Date of Patent: Mar. 28, 2017

(54) SYSTEMS, METHODS AND DEVICES FOR ANATOMICAL REGISTRATION AND SURGICAL LOCALIZATION

(71) Applicant: INTELLIJOINT SURGICAL INC., Waterloo (CA)

(72) Inventors: Andre Novomir Hladio, Hamilton (CA); Armen Garo Bakirtzian, Kitchener (CA); Richard Tyler Fanson, Stoney Creek (CA); Eric Ryterski, Louisville, CO (US)

(73) Assignee: INTELLIJOINT SURGICAL INC., Waterloo (CA)

( * ) Notice: Subject to any disclaimer, the term of this patent is extended or adjusted under 35 U.S.C. 154(b) by 0 days.

(21) Appl. No.: 15/148,084

(22) Filed: May 6, 2016

(65) Prior Publication Data

US 2016/0249987 A1    Sep. 1, 2016

Related U.S. Application Data

(63) Continuation of application No. PCT/CA2015/000558, filed on Oct. 29, 2015.

(60) Provisional application No. 62/072,041, filed on Oct. 29, 2014, provisional application No. 62/072,030, filed on Oct. 29, 2014, provisional application No.
(Continued)

(51) Int. Cl.
*A61B 34/20* (2016.01)
*A61B 90/00* (2016.01)

(52) U.S. Cl.
CPC ...... *A61B 34/20* (2016.02); *A61B 2034/2055* (2016.02); *A61B 2034/2057* (2016.02); *A61B 2034/2068* (2016.02); *A61B 2034/2072* (2016.02); *A61B 2090/067* (2016.02); *A61B 2090/3983* (2016.02)

(58) Field of Classification Search
CPC ............ A61B 34/20; A61B 2034/2055; A61B 2034/2072; A61B 2090/067
USPC .......................................................... 606/102
See application file for complete search history.

(56) References Cited

U.S. PATENT DOCUMENTS

| 6,285,902 B1 * | 9/2001 | Kienzle, III ............. A61B 6/12 378/20 |
| 2006/0190011 A1 * | 8/2006 | Ries ................... A61B 17/1666 606/130 |
| 2010/0069919 A1 | 3/2010 | Carls et al. |

FOREIGN PATENT DOCUMENTS

| WO | 2006075331 A2 | 7/2006 |
| WO | 2006128301 A1 | 12/2006 |

OTHER PUBLICATIONS

International Search Report Mailed Feb. 5, 2016 for Related International PCT Patent Application No. PCT/CA2015/000558.
(Continued)

*Primary Examiner* — Christopher Beccia
(74) *Attorney, Agent, or Firm* — Gowling WLG (Canada) LLP

(57) ABSTRACT

Systems, methods and devices are disclosed for use in electronic guidance systems for surgical navigation to determine the relationship between the three-dimensional coordinates of an anatomy of a patient and those of an electronic guidance system. These coordinates are required to assist in the determination of the angles with respect to which components, such as, an acetabular prosthesis, are inserted into a body of the patient. In one such example, during hip replacement surgery, a surgeon receives guidance of how to place an acetabular prosthesis in the body of the patient, specifically in the pelvis.

20 Claims, 15 Drawing Sheets

Related U.S. Application Data

62/072,032, filed on Oct. 29, 2014, provisional application No. 62/084,891, filed on Nov. 26, 2014.

(56) References Cited

OTHER PUBLICATIONS

Written Opinion Mailed Feb. 5, 2016 for Related International PCT Patent Application No. PCT/CA2015/000558.

* cited by examiner

| Difference from captured registration | |
|---|---|
| Pitch | +1° |
| Roll | -5° |
| Yaw | +0° |

1801
Measure a direction of gravity using a sensor, sensor comprising optical sensor and inclinometer, attached to patient anatomy in known orientation with respect to gravity

1802
Measure a direction of an axis of a device, device having a shape defining at least one axis using positional information in up to 6DOF provided by a target to the optical sensor, and known positional relationship between target and device

1803
Construct a registration coordinate frame to register anatomy during surgery based on direction of gravity, direction of axis, and known orientation of patient with respect to gravity

Figure 18

SYSTEMS, METHODS AND DEVICES FOR ANATOMICAL REGISTRATION AND SURGICAL LOCALIZATION

CROSS-REFERENCE TO RELATED APPLICATIONS

This application claims priority to U.S. provisional application No. 62/072,041 titled "Systems, Methods and Devices for Anatomical Registration and Surgical Localization" and filed on Oct. 29, 2014, the entire contents of which are incorporated herein by reference.

This application claims priority to U.S. provisional application No. 62/072,030 titled "Devices including a surgical navigation camera and systems and methods for surgical navigation" and filed on Oct. 29, 2014, the entire contents of which are incorporated herein by reference.

This application claims priority to U.S. provisional application No. 62/084,891 titled "Devices, systems and methods for natural feature tracking of surgical tools and other objects" and filed on Nov. 26, 2014, the entire contents of which are incorporated herein by reference.

This application claims priority to U.S. provisional application No. 62/072,032 titled "Devices, systems and methods for reamer guidance and cup seating" and filed on Oct. 29, 2014, the entire contents of which are incorporated herein by reference.

FIELD

The present specification relates to systems, methods and devices for use in registration of an anatomy of a patient during surgery, for surgical navigation.

BACKGROUND

A human hip joint is a ball and socket joint comprising the head of a femur bone (femoral head) located in an acetabulum of a human pelvis. During total hip arthroplasty (THA), the hip joint of a patient is replaced with prosthetic components. The surgical procedure involves the surgical excision of the head and proximal neck of the femur bone and removal of the acetabular cartilage and subchondral bone. An artificial canal is created in the proximal medullary region of the femur, and a metal femoral prosthesis is inserted into the femoral medullary canal. An acetabular component or implant is inserted proximally in the enlarged acetabular space.

One of the most important aspects of THA is ensuring proper alignment of the acetabular component or implant with respect to the pelvis. Alignment of the prosthetic components has typically been performed relying solely on a surgeon's judgment of the spatial location of the prosthetic components. Studies have shown that failure to properly align the acetabular component or implant with the pelvis may lead to premature wear, propensity to dislocate and patient discomfort. Surgical navigation systems can assist surgeons in providing guidance in the placement of the prosthesis in the body of the patient to improve clinical outcomes.

BRIEF SUMMARY

This specification describes methods, systems and devices used to register the body of the patient to an electronic guidance system for surgical navigation. During surgery guided by electronic navigation, a surgeon typically has to determine a correlation between the coordinate reference frame of a patient and that of the electronic guidance system for surgical navigation. This allows the surgeon to use his/her clinical judgment when viewing the measurements and deciding the final placement of objects, such as a hip prosthesis, in the body of the patient. The surgical navigation system needs to know the correlation so that measurements can be provided in one or both coordinate frames.

There is disclosed a system to provide intra-operative guidance during THA. The system comprises: a sensor configured to attach to an anatomy of a patient, positioned in a known orientation with respect to gravity, and comprising an optical sensor to generate optical measurements and an inclinometer to generate inclination measurements; a target configured to provide positional information to the optical sensor, the optical sensor generating the optical measurements using the positional information in up to six degrees of freedom; a device attached to the target, the device having a shape defining at least one axis, wherein the at least one axis is in a known positional relationship with the target; and an intra-operative computing unit in communication with the sensor. The intra-operative computing unit is configured to: measure a direction of at least one axis using the optical measurements from the sensor and the known positional relationship between the target and the device; measure a direction of gravity based on the inclination measurements; and construct a registration coordinate frame to register the anatomy of the patient during surgery to provide surgical navigation based on the direction of gravity, the direction of the axis and the known orientation of the patient with respect to gravity. The intra-operative computing unit is further configured to calculate, in real-time, a difference in the optical measurements in at least one degree of freedom provided by the optical sensor with respect to the registration coordinate frame and to provide the difference for display by a display unit. A sensor configured to attach to an anatomy of a patient, the anatomy being a pelvis. The device may be removably attached to the target.

There is disclosed a medical navigational guidance system wherein the intra-operative computing unit is further configured to construct the common frame of reference using a rigid mechanical relationship between the optical sensor and the inclinometer. The intraoperative computing unit is further configured to construct the registration coordinate frame using redundant measurement information wherein the redundant measurement information is used to compute a metric representing the consistency between the inclination measurements and optical measurements received from the sensor; and provide the metric to a display unit for displaying to a surgeon. The sensor is configured to generate optical measurements and inclination measurements relative to a common frame of reference.

There is disclosed a system for providing navigational guidance during THA. The system comprises: a sensor configured to attach to an anatomy of a patient, comprising an optical sensor to generate optical measurements and an inclinometer configured to generate inclination measurements; a target configured to provide positional information to the optical sensor, the optical sensor generating the optical measurements using the positional information in up to six degrees of freedom; a probe attached to the target, the probe having a tip, wherein the tip is in a known positional relationship with the target; and an intra-operative computing unit in communication with the sensor. The intra-operative computing unit is configured to: determine a location of two or more anatomical features of the patient, the features lying on the anterior pelvic plane of the patient, using optical measurements of the sensor and the known positional relationship between the target and the tip of the probe; calculate a direction of at least one axis defined by the location of the two or more anatomical features; and construct a registration coordinate frame to register, during surgery, the anatomy of the patient based on the direction of gravity and the direction of the axis. The intra-operative computing unit is further configured to generate a secondary registration coordinate frame by localizing three anatomical features on the acetabular rim of the patient. The system is configured to provide navigational guidance based on the registration coordinate frame and the secondary registration coordinate frame. A sensor configured to attach to an anatomy of a patient, the anatomy being a pelvis. The probe may be removably attached to the target.

There is disclosed a computer-implemented method for a medical navigation guidance system capable of: measuring, by at least one processing unit, a direction of gravity using a sensor, the sensor comprising an optical sensor and an inclinometer, attached to an anatomy of a patient positioned in a known orientation with respect to gravity; measuring, by at least one processing unit, a direction of an axis of a device, the device having a shape defining at least one axis using positional information in up to six degrees of freedom provided by a target to the optical sensor, and a known positional relationship between the target and the device; and constructing, by at least one processing unit, a registration coordinate frame to register, during surgery, the anatomy of the patient based on the direction of gravity, the direction of the axis and the known orientation of the patient with respect to gravity. When the patient is positioned in a second orientation, the intra-operative computing unit is further configured to provide surgical navigation based on the registration coordinate frame.

There is disclosed a medical navigational guidance system comprising: a sensor comprising an optical sensor configured to generate optical measurements and an inclinometer configured to generate inclination measurements; a first target attached to an anatomy of a patient configured to provide positional signals in up to six degrees of freedom to the optical sensor; a second target configured to provide positional information in up to six degrees of freedom to the optical sensor and configured to be attached to a device with a shape that defines at least one axis, wherein the at least one axis has a known positional relationship with the second target; and an intra-operative computing unit. The sensor is configured to attach to an operating table. The sensor is further configured to be held in the hand of a surgeon. The intra-operative computing unit is configured to: receive positional signals of the first target from the optical sensor; receive inclination measurements from the inclinometer; calculate position and orientation of the first target; calculate the direction of gravity with respect to the position and orientation of the first target based on the inclination measurements; measure the direction of the at least one axis using positional information provided by the second target and the known positional relationship between the second target and the device; and construct a registration coordinate frame for the anatomy of the patient based on the direction of gravity with respect to the first target, position and orientation of the first target and the direction of the axis.

BRIEF DESCRIPTION OF DRAWINGS

Embodiments disclosed herein will be more fully understood from the detailed description and the corresponding drawings, which form a part of this specification, and in which:

FIG. 6 is a screenshot of a representative verification feature in a display unit of a workstation of the electronic guidance system in accordance with an embodiment;

FIG. 18 is a flowchart of a computer-implemented method for registration using an axis frame and inclination measurements.

It will be appreciated that for simplicity and clarity of illustration, elements shown in the figures have not necessarily been drawn to scale. For example, the dimensions of some of the elements may be exaggerated relative to other elements for clarity.

DETAILED DESCRIPTION

Systems, methods and devices are presented herein pertaining to anatomical registration and surgical localization during surgical navigation. The embodiments refer to use of an electronic guidance system in THA. However, a person skilled in the art will realize that the specification is applicable to other forms of surgery and is not meant to be limited to THA. It is further understood that various methods described for performance by a computer system such as navigational surgery may be implemented in software such as instructions and data to configure at least one processing unit of a computer system to perform the method. The instructions and data may be stored in a device such as a memory (RAM, ROM, flash drive, etc.) or other non-transitory storage device (e.g.: magnetic, optical, or other disk or storage medium).

Several systems, methods and devices will be described below as embodiments. The scope of the claims should not be limited by the embodiments set forth in the examples, but should be given the broadest interpretation consistent with the description as a whole.

Figure 1:
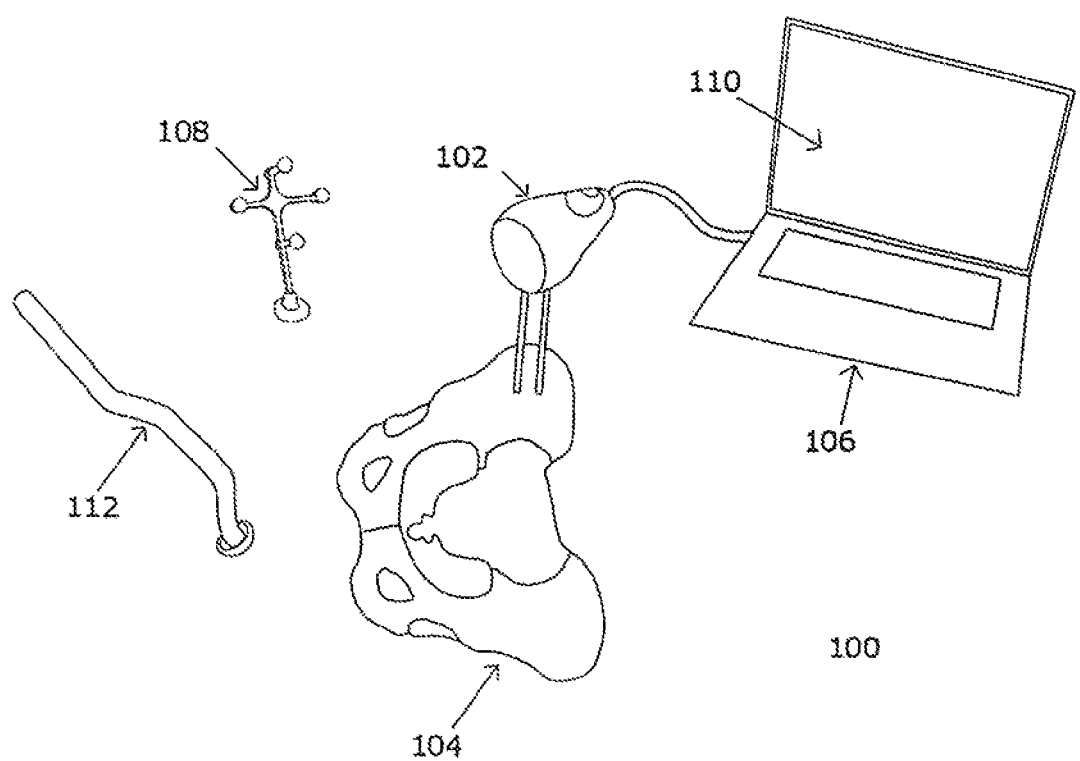
FIG. 1 shows some components of an electronic guidance system in accordance with an embodiment.

In order to provide electronic guidance with respect to the anatomy of the patient in THA, the spatial coordinates of the anatomy of the patient (e.g., the pelvis) with respect to the electronic guidance system are required. This step is referred to as "registration" in this specification. Anatomical registration pertains to generating a digital positional or coordinate mapping between the anatomy of interest and a localization system or an electronic guidance system. There are multiple methods to obtain this registration mapping or the registration coordinate frame. It is desirable that these methods of registration are fast, so as to not increase the duration of the surgical workflow, and sufficiently accurate. The electronic guidance system utilizes the registration coordinate frame to intra-operatively provide clinically relevant measurements to the surgeon using the system. FIG. 1 illustrates an electronic guidance system 100 used in THA where a sensor 102 is attached an anatomy of a patient (e.g. a pelvis 104) and communicates with a workstation or an intra-operative computing unit 106. The pose (position and orientation) of a target 108 can be detected by the sensor 102 and displayed on a graphical user interface (GUI) 110 of the workstation 106. The target 108 may be attached to an instrument 112 or to another part of the anatomy of the patient (e.g. to a femur).

Pelvic registration, particularly useful in THA, is selected as an exemplary embodiment; however, this description is intended to be interpreted as applicable to general anatomy and in various other surgeries.

In this disclosure, normally a sensor is attached to a bone of the anatomy of the patient or a steady surface such as an operating table. A target, detectable by the sensor in up to six degrees of freedom, is located on an object being tracked, such as another bone of the anatomy of the patient, a tool, a prosthesis, etc. However, in general, the locations of the sensor and target can be reversed without compromising functionality (e.g. fixing the target on the bone or a steady surface and attaching the sensor to the object to be tracked), and this disclosure should be interpreted accordingly.

Furthermore, one skilled in the art will appreciate that the techniques, components, and methods described herein may be implemented using different tracking modalities. For example, use of traditional stereoscopic localization cameras (e.g. the Polaris™ product from Northern Digital Inc. in Waterloo, ON), electromagnetic tracking systems (e.g. the Aurora™ product from Northern Digital Inc), ultrasonic localizers (e.g. see U.S. Pat. No. 8,000,926), mechanical localization devices. RF localizers, etc. are contemplated.

Figure 2:
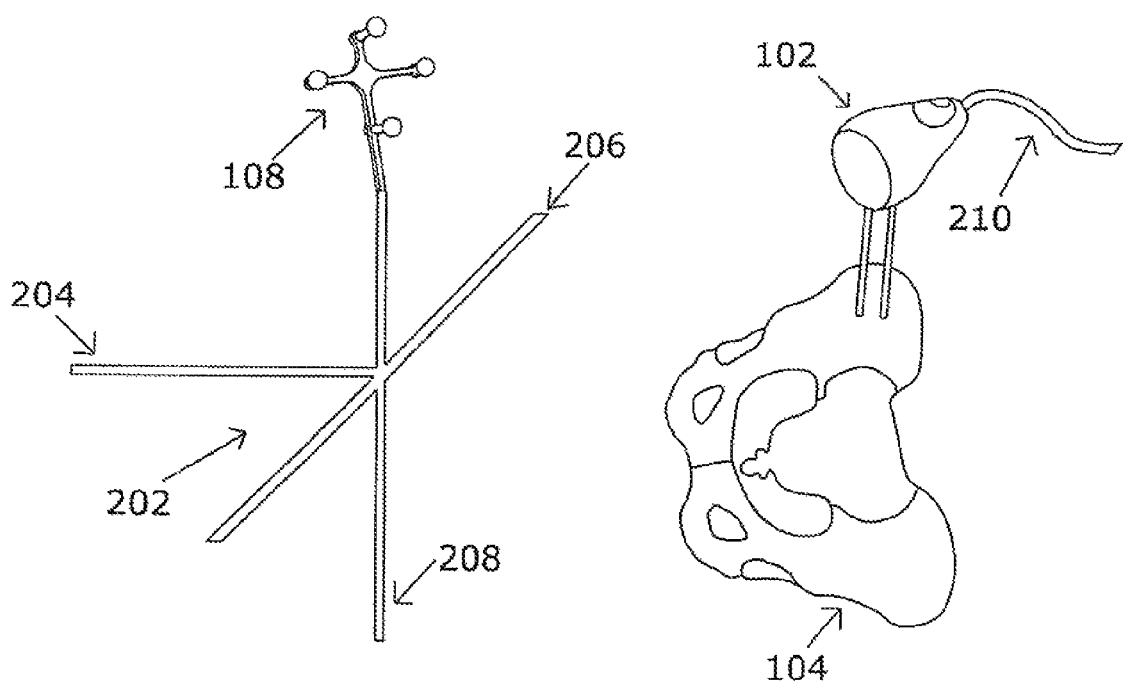
FIG. 2 shows an axis frame used in registration of an of a patient to that of the electronic guidance system for surgery in accordance with an embodiment.

Reference is now made to FIG. 2, which illustrates a device 202, referred to as an axis frame that may be used to register an anatomy of a patient. Through its shape, an axis frame 202 can define axes, such as a first axis 204, a second axis 206 and a third 208 axis. For example, an axis frame may be comprised of three orthogonal bars (204, 206, and 208) that define three axes. The sensor 102 is attached to the pelvis of the anatomy 104 of the patient and communicates with an intra-operative computing unit 106 through a cable 210. The sensor may comprise an optical sensor to track positional information of the target 108 attached to the axis frame 202. This information is used to measure the directions of the anatomical axes of a patient in order to construct the registration coordinate frame. At the time of use, the positional relationship between the axes of the axis frame 202 and the target 108 must be known to the intra-operative computing unit 106, either through precise manufacturing tolerances, or via a calibration procedure. This relationship is vital to determining the registration coordinate frame. Generally, surgical grade metals are used to manufacture devices such as, an axis frame, as these metals are biocompatible and can be sterilized in a hospital setting.

Figure 3:
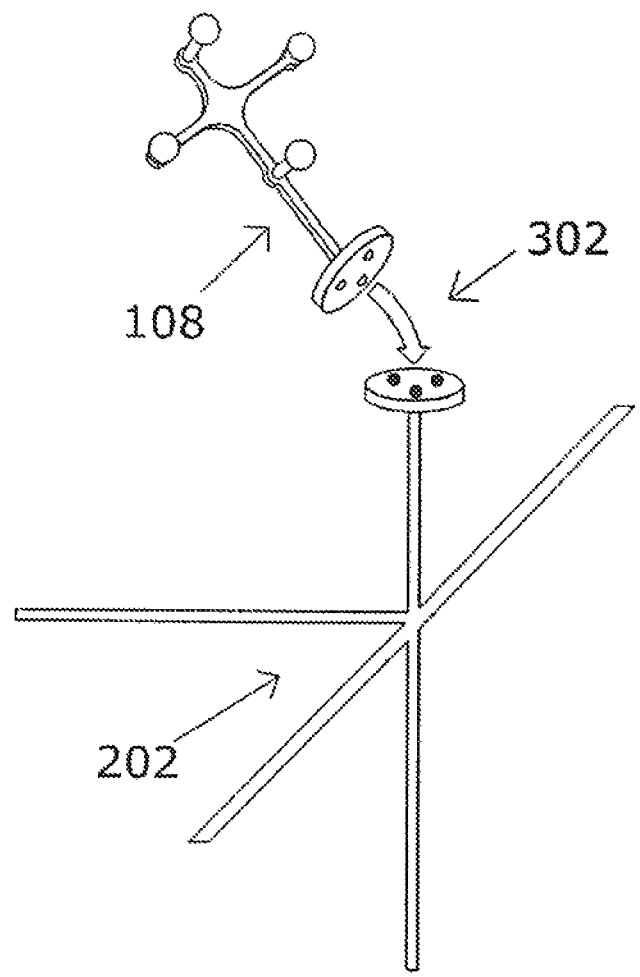
FIG. 3 shows a target member removably attached to an axis frame in accordance with an embodiment.

Rather than have a dedicated target for the axis frame, it may be advantageous to provide a removable target, such that the same target may be used to track a variety of instruments, implants and/or objects. The axis frame may have a target that is removably or integrally affixed to the axis frame and that can be tracked by the optical sensor. This is illustrated in FIG. 3, where the target 108 may be detached from the body of the axis frame 202, and may be coupled via a repeatable mount or quick connect mechanism 302, such as the one taught in U.S. 20140275940 titled "System and Method for Intra-Operative Leg Position Measurement" and filed on Mar. 15, 2013, the entire contents of which are incorporated herein by reference. The quick connect mechanism 302 is repeatable and accurate to ensure that the pose of the target 108 repeatably and accurately relates to the pose of the axis frame 202 in a pre-determined mathematical relation.

Figure 4:
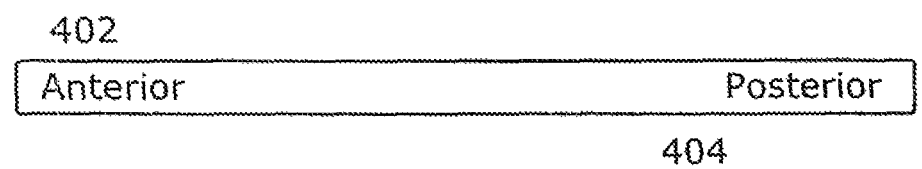
FIG. 4 shows labels on one of the axes of an axis frame as an example for clarity.

In addition to the shape of the axis frame that defines the axis/axes of interest for the purpose of registration, clinically relevant markings or labels may be used to define how the axis frame is intended to be aligned. In FIG. 4, for example, if a straight bar is used in an axis frame to define the anterior-posterior direction on a patient it may be labeled accordingly with an anterior label 402 and a posterior label 404.

An important aspect of the design of the axis frame is that it is trackable when in alignment with the anatomy. When the axis frame is aligned with the patient, the target must be within the field of view of the camera or sensor. This aspect may take into account patient-to-patient anatomical variations, as well as variations in the positioning of the sensor on the pelvis.

Figure 5:
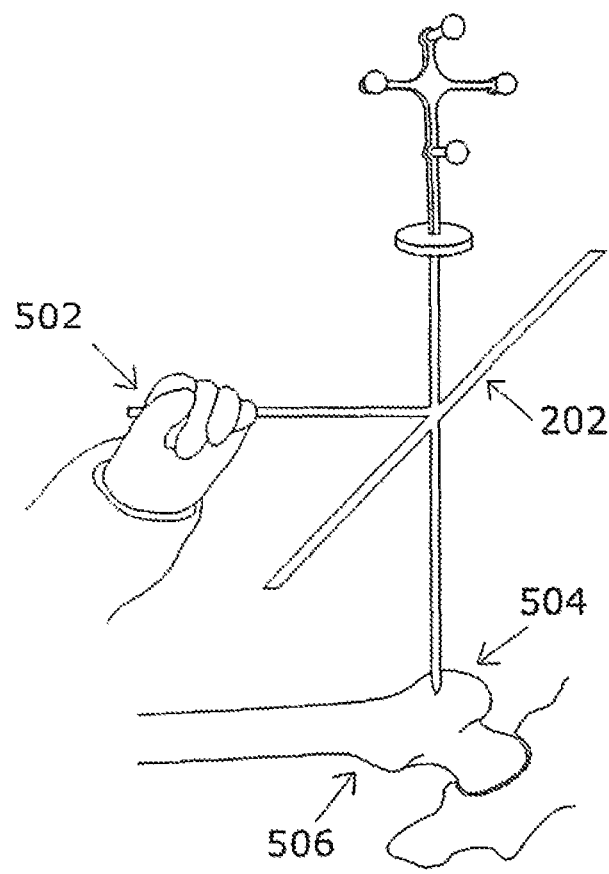
FIG. 5 shows the axis frame resting on a femur bone of a patient as an example for clarity.

Since the axis frame requires a user to manipulate it into the correct position with respect to the anatomy, ergonomic considerations for the user are important. In one embodiment as illustrated in FIG. 5, a hand 502 of a user is depicted holding an axis frame 202 with a contact point 504 resting on a femur 506 during a pelvic registration. A member comprising the contact point 504 may be at an additional attachment to the axis frame 202 such that it is attached only if and when required during the surgical workflow. The contact point 504 may be located at the tip of any of the axes of the axis frame 202. The purpose of the contact point 504 is to allow a user to manually rest the axis frame on a stable point such that the axis frame 202 is easier to manually align with the anatomy of interest. It is easier to align something when it is partially stabilized. The contact point 504 may be within a surgical wound, or outside. The location of the contact point 504 is not required to be repeatable.

A verification feature may be provided in the intra-operative computing unit. For example, after the registration coordinate frame has been calculated, the axis frame may continue to be tracked as it is manipulated by a user (e.g. a surgeon). As shown in FIG. 6, a GUI 110 on a display unit may update in real-time a current position of the axis frame relative to the registered position or coordinate frame. In this case, a metric, such as the three-dimensional difference in orientation, is depicted. Fewer degrees of freedom may also be depicted. This verification feature provides real-time feedback to the user, and allows the user to assess confidence in the positioning of the axis frame for registration. The computing unit may also allow the user to re-do the step of registration, should the user choose to do so. Although a numerical display is shown in FIG. 6, it may be preferable to include a graphical display, such as a bulls-eye graphic. The computing unit may provide guidance on how to move the axis frame in order to return to the original registered position.

The verification feature also allows a user to verify and/or redo the registration steps at any point during the surgical procedure. It is preferable to perform the registration as soon as possible after the patient has been positioned and draped for surgery, such that the orientation of the anatomy (e.g. the pelvis) is known. The patient may then be moved (deliberately or unintentionally) as part of the surgical workflow without compromising the registration. Since the surgeon is typically involved in the preparation and draping, the surgeon will have a spatial awareness of the anatomical positioning of the patient with respect to the ground or to the operating table or to any other stationary object, even if the body of the patient is obscured by surgical draping. Furthermore, in many surgeries, the anatomy of the patient may shift or purposefully be moved as the surgeon may be required or may choose to position the patient into various positions. Registering the anatomical coordinate frame of the patient as soon as possible after patient positioning may eliminate patient shifting as a source of measurement error.

In many surgical procedures, such as THA, care is taken in patient positioning at the beginning of surgery. For example, whether in lateral decubitus or supine positioning, surgeons often ensure that the patient is in a known position with respect to the horizontal plane (referring to the plane orthogonal to gravity). The knowledge of the position of the patient with respect to the horizontal plane is often used as an aid in positioning implants. The ability to electronically measure the horizontal plane has several advantages. This information may be used to aid anatomical registration (i.e. taking advantage of the care taken when positioning patients). The horizontal plane may be registered at the commencement of the surgical procedure, with a low likelihood of the anatomy of the patient having shifted under the surgical draping.

Figure 7:
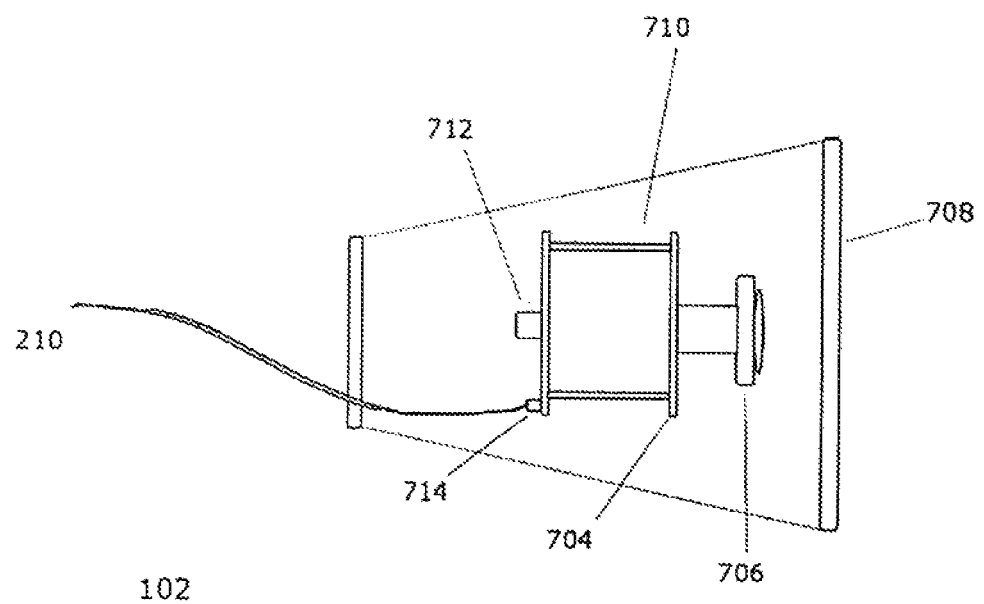
FIG. 7 shows a cross-section of a sensor with optical and inertial sensing components in an electronic guidance system as an example for clarity.

Incorporating inclination sensing that can assist in the determination of the horizontal plane may be accomplished, for example, by adding an inclinometer (or accelerometer) into the sensor, as depicted in FIG. 7. The sensor 102 comprises an optical sensor (a camera 704 comprising a lens 706, an optical window 708, etc.) that is connected by a rigid structure 710 to an inclinometer 712. The sensor 102 is also connected via a connector 714 and a cable 210 to a workstation 106. In this case, the sensor 102 provides optical and inclination measurements, both related to a common frame of reference. Further discussion on how to enable this is provided below.

Figure 8:
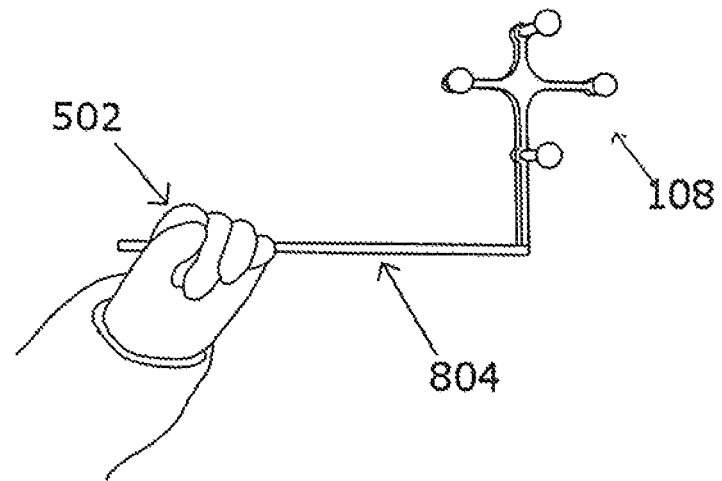
FIG. 8 shows an axis frame with a single axis as an example for clarity.

Often, three degrees of freedom in orientation are needed to register the anatomy. Inclination measurements provide two degrees of freedom in orientation. The inclination measurements may be used for construction of the registration coordinate frame. For example, if an anatomy of a patient has a known position with respect to the horizontal plane, the sensor (attached to the anatomy or to a stable location, such as, the operating table) measures the horizontal plane, and the intra-operative computing unit uses this information as part of anatomical registration. Using inclination measurements to provide up to two degrees of freedom, the third degree of freedom may be measured from an axis frame, configured to provide a single axis. As in FIG. 8, a hand 502 of a user is shown holding an axis frame 202 with a single axis 804 and a target 108 attached to it. During registration, the single axis may be aligned anywhere within the plane of the final degree of freedom.

It may be the case that the anatomy of the patient has a known position with respect to only one degree of freedom of the horizontal plane. In this case, two additional degrees of freedom from an axis frame may be required to enable registration of the anatomy. The axis frame with a single axis and a target affixed to it may define at least two degrees of freedom in orientation. The registration coordinate frame may then be constructed by utilizing all three degrees of freedom.

Furthermore, it may be beneficial to generate redundant information required for the registration step. Redundant information can be obtained from a full registration using an axis frame and inclination measurements to capture the same degrees of freedom. Redundant registration information may be beneficial for error checking, or for using an optimization routine to register the anatomy of the patient based on the aggregate information. This information, in the form of a metric, may be displayed to the user or may be used to represent the consistency between the measurements obtained from the inclination system and the optical sensor.

According to a preferred method wherein inclination measurements and optical measurements are used to define a registration, the inclination measurements and the optical measurements may be captured or measured substantially contemporaneously.

An axis may also be defined by capturing (or "localizing") two discrete points. A device such as a probe, with a tip that is in a known positional relationship with the target affixed to it, may be used to determine the location of two or more anatomical features of interest. The position of the tip of the probe may be captured by the electronic guidance system as a part of the registration of the anatomy. The two discrete points (in three-dimensional space) localized by the probe define a vector (analogous to how any one axis of an axis frame defines a vector). For example, the discrete point may be the ASIS (anterior superior iliac spine) of a pelvis, which is a commonly utilized anatomical location for registration.

Figure 9:
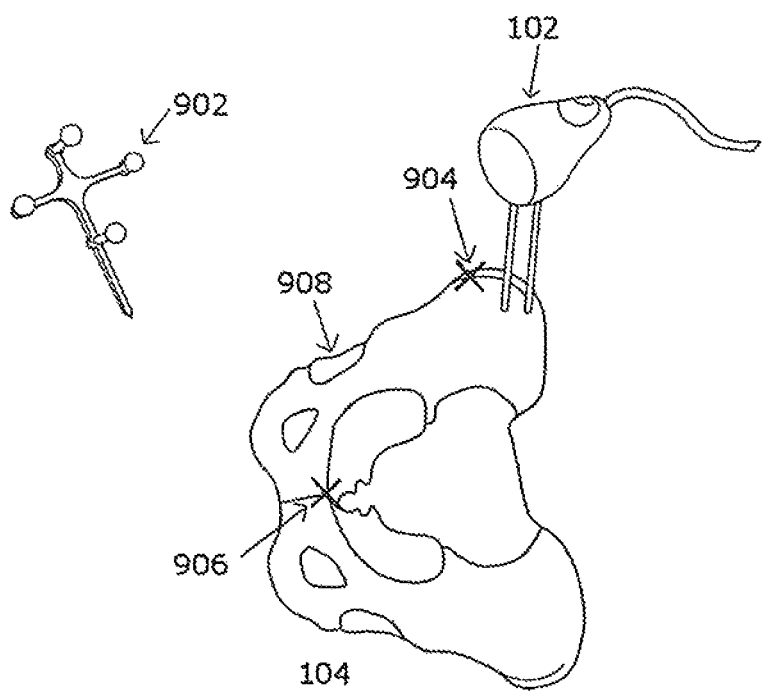
FIG. 9 shows a patient positioned laterally, with a sensor of an electronic guidance system attached to the anatomy of the patient, and a probe to capture locations of landmarks as an example for clarity.

There are various surgical approaches in THA, such as the posterior approach, anterior approach, etc. that require the patient to be positioned in lateral decubitus or supine. The anterior pelvic plane (APP) of the anatomy is comprised of both ASIS locations and the pubic symphysis, and is often used for registration of the pelvis in different surgical approaches. Accessing points that define the anterior pelvic plane can be challenging when a patient is positioned in lateral decubitus, since the location of the contralateral ASIS is obscured and difficult to access for the surgeon. However, if the pelvis is positioned substantially vertically with respect to the operating table or the horizontal plane, this obviates the need to access the contralateral ASIS. It is sufficient to localize two points, such as, the operative ASIS, and the pubis using a probe. These points lie in the frontal plane of the pelvis, and, in combination with inclination measurements (which provide the third degree of freedom), the pelvic registration coordinate frame may be constructed. FIG. 9 illustrates a sensor 102 attached to the pelvis 104 of the patient when the patient is positioned laterally. The target 108 attached to a probe 902 can be used to localize landmarks like the operative ASIS 904 and the pubis 906 or locations within the acetabulum 908. The probe 902 is illustrated to be unitary with the target 108. However, this is not a limitation of this embodiment. The target 108 may be removably attached to the probe 902. The workstation measures the position and orientation of the tip of the probe 902 using positional information from the target 108 to determine the location of the landmarks.

Figures 10, 11:
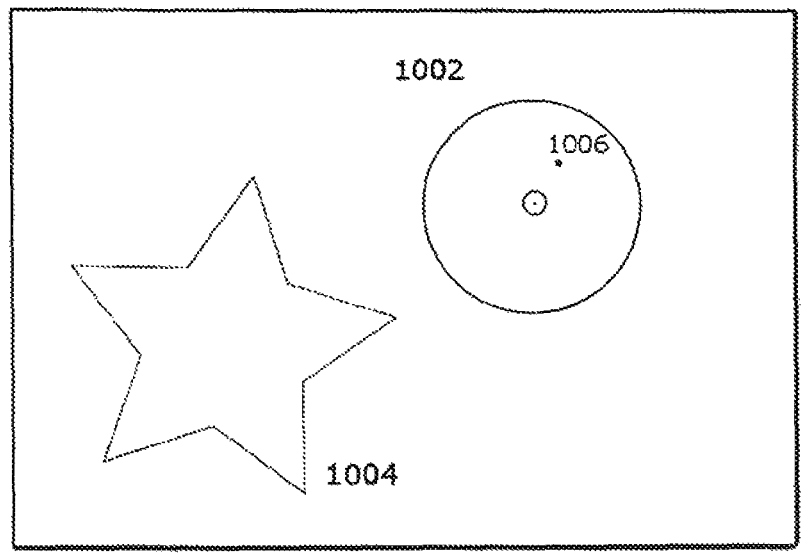
FIG. 10 is a screenshot of a representative bubble level graphic updating in real-time on a display unit of a workstation of an electronic guidance system.
FIG. 11 is a screenshot of a display unit of a workstation showing measurements in internal and external reference coordinate frames in accordance with an embodiment.

In one embodiment, the inclination measurements of the sensor are provided to the surgeon in real-time to track patient motion during the procedure. These measurements may be provided to a surgeon (e.g. persistently) via the GUI on the display unit. As illustrated in FIG. 10, for example, the measurements may be conveyed as a bubble level graphic 1002 where the graphic may be persistently in real-time or selectively displayed, in addition to other GUI content 1004. The inclination measurements may be displayed relative to the measurements captured during registration such that the bubble 1006 is centered in the graphic 1002 when the current inclination matches the inclination measured at registration. Furthermore, the direction of the bubble level 1006 may utilize the registration coordinate frame such that the current inclination is expressed with respect to the anatomical directions of the body of the patient. As an example, if the bubble moves to the right on the screen, this may have a physical relationship to how the patient may have shifted.

In order to provide inclination measurements, an accelerometer may be integrated within the sensor, as shown in FIG. 7. The optical sensor of the sensor comprises an optical window 708, a camera 704 comprising a lens 706. The accelerometer measurements are combined with optical measurements using techniques known in the art of sensor fusion, such that measurements are provided with a common frame of reference. A rigid structure 710 exists between the location of the camera and the accelerometer, thus creating a rigid mechanical relationship. This relationship is unique for each physical device and is used by the workstation when both the accelerometer 712 and camera 704 communicate measurements to it by any means. e.g. wired through a cable 210, wireless, etc. The workstation may use this relationship to align inclinometer coordinate values to the optical coordinate values, and display further calculations in the same frame of reference.

In addition or alternative to accelerometers, other sensing components may be integrated to assist in registration and/or pose estimation. Such sensing components include, but are not limited to, gyroscopes, inclinometers, magnetometers, etc. It may be preferable for the sensing components to be in the form of electronic integrated circuits.

Both the axis frame and the accelerometer may be used for registration. The optical and inclination measurements captured by the system rely on the surgeon to either accurately position the patient, or accurately align the axis frame along the axis/axes of an anatomy of a patient, or both. It may be desirable to provide further independent information for use in registering the anatomy of the patient. For example, in THA, the native acetabular plane may be registered by capturing the location of at least three points along the acetabular rim using a probe attached to a trackable target. When positioning implants with respect to the pelvis, information may be presented with respect to both registrations—one captured by the workstation from optical measurements of the axis frame and inclination measurements (primary registration coordinate frame), and the other captured by the workstation using the reference plane generated from the optical measurements of the localized landmarks on the acetabular rim of the patient (secondary registration coordinate frame)—either in combination, or independently.

FIG. 11 shows a GUI on a display unit. In this embodiment, the interface splits the screen into two sections—an Internal Reference 1102 and an External Reference 1104. The Internal Reference 1102 presents a frame of reference with respect to the internal acetabular landmarks that were independently captured in the construction of the registration coordinate frame as the native anatomy of the patient. A graph 1106 on the GUI displays a bulls-eye indicator 1110 that represents the native acetabulum. The External Reference 1104 presents data to the surgeon in a registration coordinate frame defined by the measuring of the horizontal plane and/or axis frame. The surgeon may use their clinical judgment in interpreting the data and taking appropriate action. In this example, the clinical measurements presented are for real-time acetabular cup alignment in THA.

Figure 12:
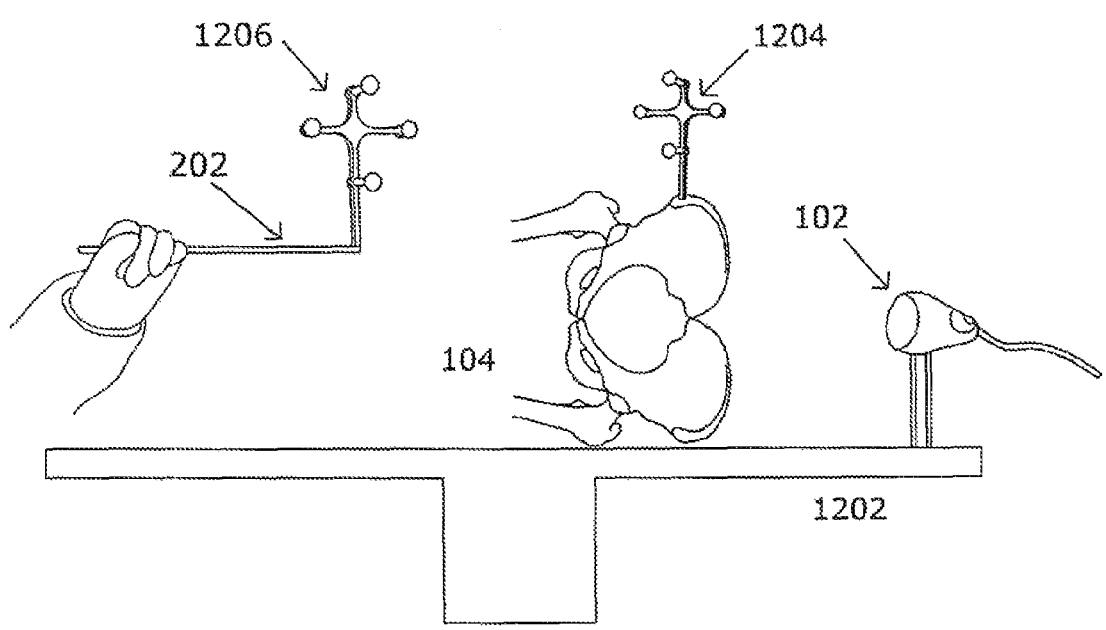
FIG. 12 shows an anatomy of a patient and a sensor attached to an operating table or bed to capture measurements from the axis frame as an example for clarity.

In the previous embodiments, a sensor has been attached to the anatomy of the patient that is to be registered for the surgical procedure. Each of the previous embodiments may be modified by changing the location of the sensor to another location from which it can detect the position and orientation of one or more targets. For example, the sensor may be attached to an operating table, held in the hand of a surgeon, mounted to a surgeon's head, etc. This embodiment is illustrated in FIG. 12. The sensor 102 is depicted attached to an operating room table 1202. A first target 1204 may be attached to the pelvis 104 of the patient, and a second target 1206 may be attached to a registration device (probe 902 or axis frame 202). The sensor 102 captures the position and orientation of both targets. The workstation calculates a relative measurement of position and orientation between both targets. In addition, the sensor 102 captures the inclination measurements, and the position and orientation of the first target 1204 attached to the anatomy of the patient. The workstation then calculates the direction of the gravity with respect to the first target 1204. Using the relative pose measurement between both targets, and the direction of gravity with respect to the first target 1204 attached to the anatomy of the patient, the workstation can construct the registration coordinate frame.

Figure 13:
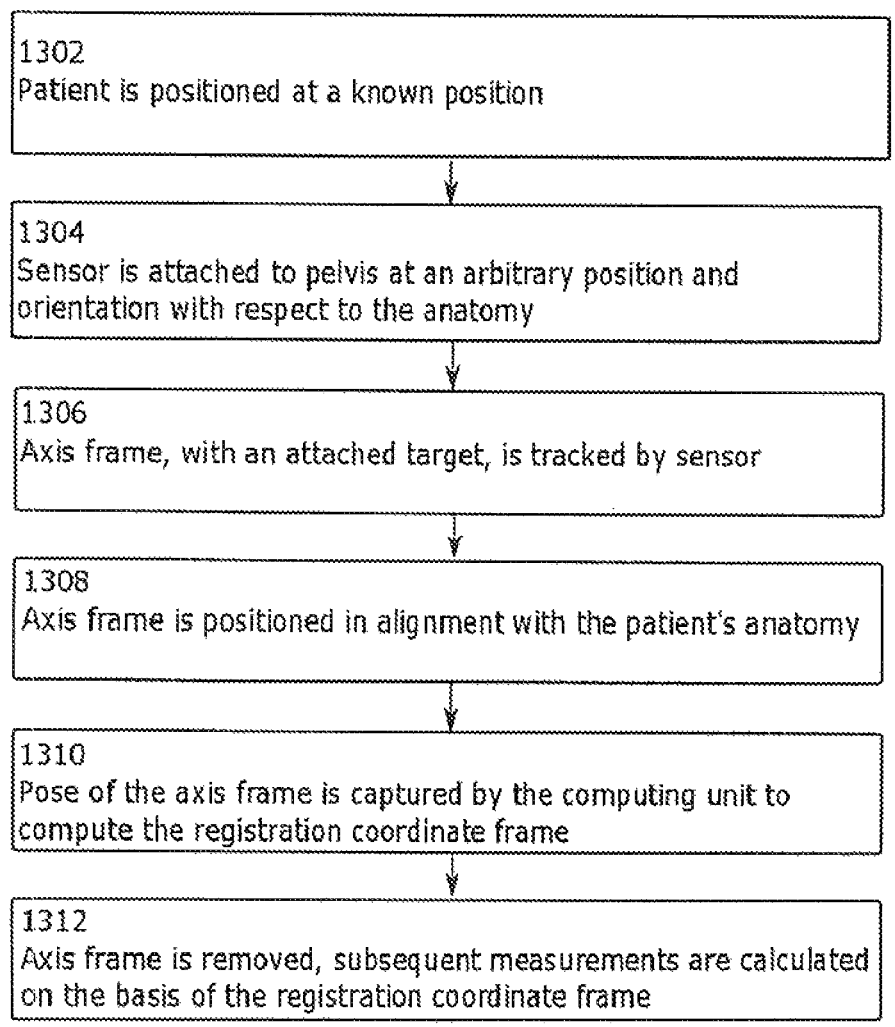
FIG. 13 is a flowchart of a method for registration using a registration device.

An exemplary method of use as shown in the flowchart of FIG. 13 may include the following: at step 1302, a patient is positioned, the position being known to the surgeon. At step 1304, a sensor is rigidly attached to the pelvis at an arbitrary position and orientation with respect to the anatomy. At step 1306, an axis frame, with a trackable target, is tracked by the sensor. At step 1308, when the axis frame is positioned in alignment with the known position of the patient's anatomy by the surgeon, step 1310 is carried out the computing unit to capture the pose of the axis frame by. This pose is used to compute a registration coordinate frame between the sensor and the anatomy. At step 1312, the axis frame is removed and/or discarded, and subsequent positional measurements of the localizer system are calculated on the basis of the registration coordinate frame.

Various methods, devices and systems for anatomical registration are presented herein. The following provides an exemplary workflow illustrating their practical usage in the context of THA. These steps are to provide an exemplary workflow, and not all of the steps are mandatory. For example, if a surgeon is not interested in leg position measurement, the corresponding steps may be omitted.

Figure 14:
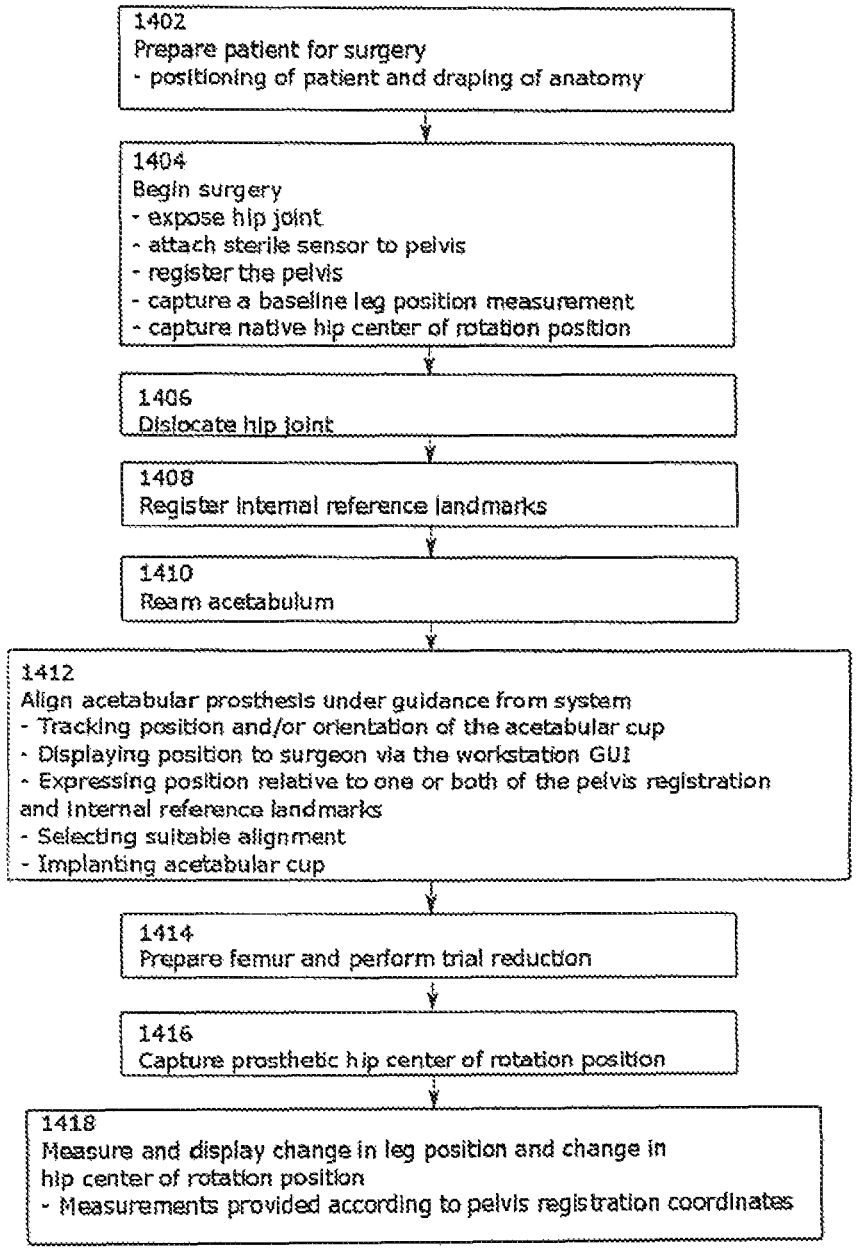
FIG. 14 is a flowchart of a method for total hip arthroplasty using an electronic guidance system in accordance with an embodiment.

As shown in FIG. 14, the flowchart illustrates the steps involved in the overall workflow of TI-IA. The first step 1402 involves preparing a patient for surgery, including positioning and draping. The surgery begins at step 1404 in which the surgeon (in no particular order) attaches the sterile sensor to the pelvis of the patient, registers the pelvis, exposes the hip joint, and captures a baseline leg position measurement and native hip center of rotation position. Those skilled in the art will understand that there are numerous methods, systems and devices available to register the patient and obtain the baseline measurements, some of which are described in the disclosure herein. The next step 1406 is to dislocate the hip joint of the patient. This is followed by step 1408 for registration of internal referencing landmarks, such as, on the acetabular rim. The surgeon then reams the acetabulum at step 1410 to create the surface that will receive the acetabular implant. The surgical navigation system is then used to align the acetabular prosthetic under guidance from the system at step 1412, by tracking the position and/or orientation of the acetabular cup, displaying measurements to the surgeon via the workstation GUI. The measurements may be expressed relative to one or both of the pelvic registration and the internal reference landmarks from the acetabular rim, and selecting a suitable alignment and implanting the acetabular cup.

At step 1414, the surgeon then prepares the femur of the patient and performs trial reductions. During the trials, at step 1416, the surgeon captures a new hip center of rotation position with the prosthetic in place. Finally, at step 1418, the workstation measures and displays change in leg position and change in hip center of rotation position, and the measurements are presented to the surgeon according to the registration coordinate frame.

Figure 15:
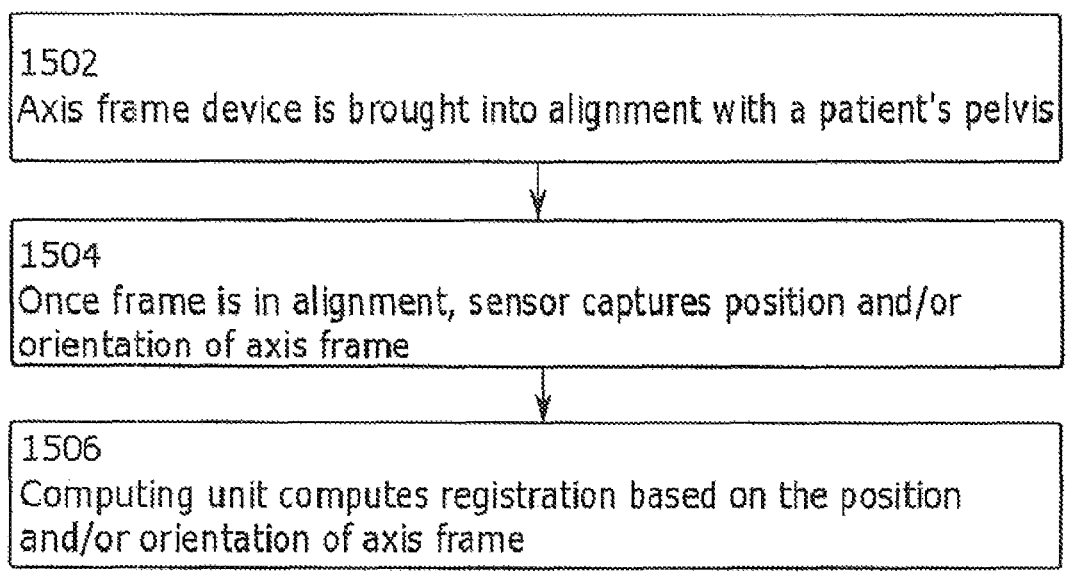
FIG. 15 is a flowchart of a method for registration using an axis frame only in accordance with an embodiment.

In an embodiment, the axis frame can be used in THA as described below in the detailed workflow options for pelvic registration. The method is described in FIG. 15. Using an axis frame at step 1502, the anatomy of the patient can be registered by bringing the axis frame, with the target attached to it, in alignment with the pelvis of the patient while the target is in the field of view of the optical sensor. At step 1504, once the user is satisfied that the axis frame is positioned appropriately with respect to the anatomy of the patient, the user initiates a capture of the position and orientation of the target in up to six degrees of freedom. This could be done, for example, through a human user interface, such as, a button. At step 1506, the intra-operative computing unit utilizes this information and computes a registration coordinate frame for the patient.

Figure 16:
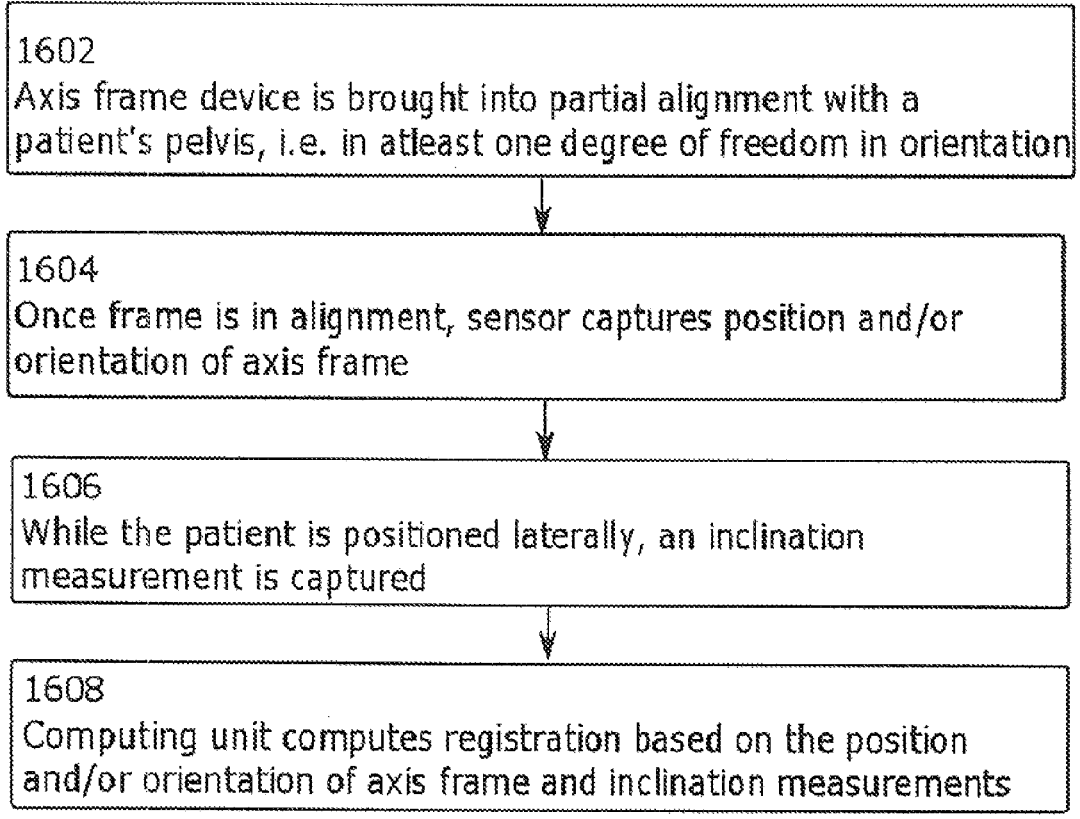
FIG. 16 is a flowchart of a method for registration using an axis frame and inclination measurements in accordance with an embodiment.

Reference is now made to FIG. 16, which illustrates a method of registration. The inclination measurements captured from an inclinometer in the sensor can provide additional measurements to the intra-operative computing unit for constructing the registration coordinate frame. At steps 1602 and 1604, measurements from the axis frame while it is positioned in alignment with the anatomy of the patient are captured and the intra-operative computing unit utilizes these measurements to compute one or two degrees of freedom of the registration measurement. At step 1606, the final degree(s) of freedom is/are captured from the inclinometer when the patient is positioned laterally on an operating table with his/her pelvis orthogonal with respect to the ground. Since the inclinometer can be housed within the optical sensor, there may be a human user interface, such as a button, to capture the optical and inclination measurements simultaneously. The two measurements can also be captured in distinct steps. Using both sets of measurements, at step 1608, the intra-operative computing unit can construct the registration coordinate frame.

Figure 17:
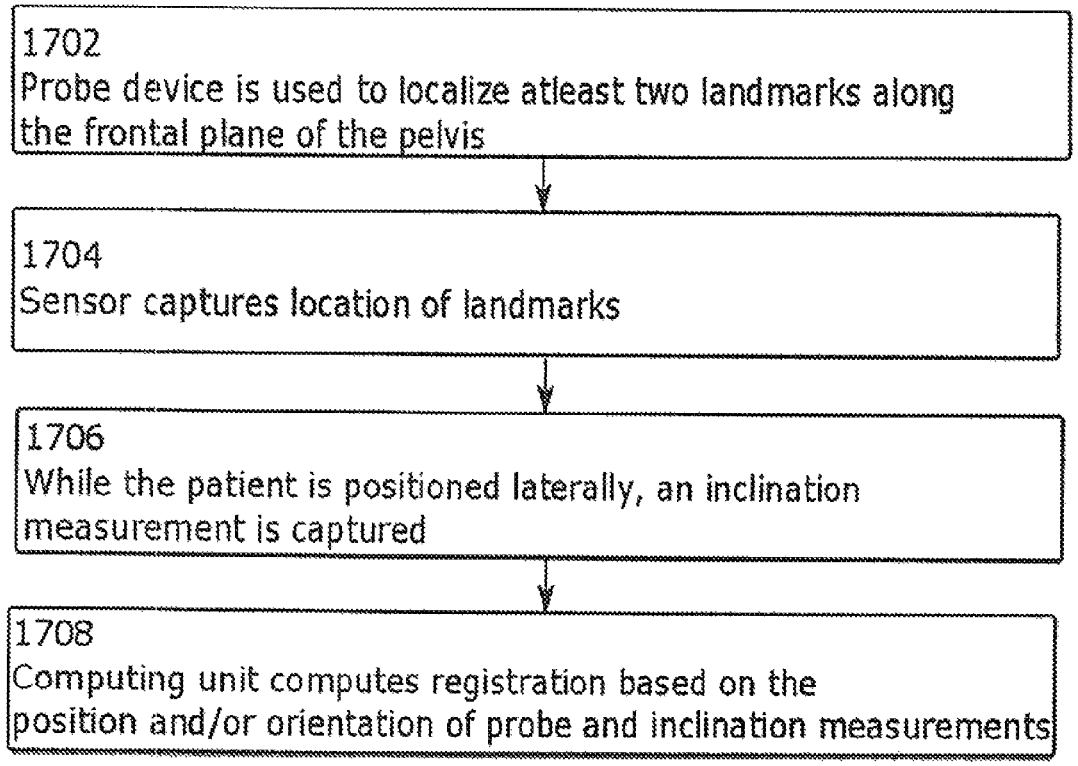
FIG. 17 is a flowchart of a method for registration using inclination measurements and localized landmarks in accordance with an embodiment.

Reference is now made to FIG. 17. Instead of using an axis frame to determine an axis of the body of the patient, at step 1702, a probe with an attached target that can be tracked by the optical sensor may be used to localize at least two anatomical landmarks that lie along an anatomical plane (e.g. frontal plane) of the pelvis, e.g.: an operative ASIS and the pubic symphysis. The location of the probe tip is in a known positional relationship with respect to the target. At step 1704, when localizing landmarks, the intra-operative computing unit captures the location of the tip of the probe as it is placed on an anatomical landmark and the optical sensor captures the positional information from the target. While the patient is positioned laterally, i.e. orthogonal to the floor, and the sensor is attached to the body of the patient such that the sensor is upright, inclination measurements are captured (such that the inclination measurements define a plane that represents the sagittal plane of the patient) at step 1706. The intra-operative computing unit is then able to compute the registration coordinate frame in three degrees of freedom based on the two localized landmarks and inclination measurements at step 1708.

Reference is now made to FIG. 18. A computer-implemented method 1800 for a medical navigation guidance system is shown in a flowchart. The method is capable of, at step 1801, measuring a direction of gravity using a sensor 102, the sensor comprising an optical sensor and an inclinometer, attached to an anatomy of a patient positioned in a known orientation with respect to gravity; at step 1802, measuring, by at least one processing unit, a direction of an axis of a device 202, the device 202 having a shape defining at least one axis using positional information in up to six degrees of freedom provided by a target 108 to the optical sensor, and a known positional relationship between the target 108 and the device 202; and at step 1803, constructing, by at least one processing unit, a registration coordinate frame to register, during surgery, the anatomy of the patient based on the direction of gravity, the direction of the axis and the known orientation of the patient with respect to gravity.

Accordingly, it is to be understood that this subject matter is not limited to particular embodiments described, and as such may vary. It is also to be understood that the terminology used herein is for the purpose of describing particular embodiments only, and is not intended to be limiting.

As will be apparent to those of skill in the art upon reading this disclosure, each of the individual embodiments described and illustrated herein has discrete components and features which may be readily separated from or combined with the features of any of the other several embodiments without departing from the teachings herein. Any recited method can be carried out in the order of events recited or in any other order which is logically possible.

What is claimed is:

1. A system comprising:
    a sensor configured to attach to an anatomy of a patient positioned in a known orientation with respect to gravity, and comprising an optical sensor to generate optical measurements and an inclinometer to generate inclination measurements;
    a target configured to provide positional information to the optical sensor, the optical sensor generating the optical measurements using the positional information in up to six degrees of freedom;
    a device attached to the target, the device having a shape defining at least one axis, wherein the at least one axis is in a known positional relationship with the target; and
    an intra-operative computing unit in communication with the sensor, the intra-operative computing unit configured to:

measure a direction of the at least one axis using the optical measurements from the sensor and the known positional relationship between the target and the device;

measure a direction of gravity based on the inclination measurements;

construct a registration coordinate frame to register the anatomy of the patient during surgery to provide surgical navigation based on the direction of gravity, the direction of the axis and the known orientation of the patient with respect to gravity.

2. The system of claim 1 wherein the device is removably attached to the target.

3. The system of claim 1 wherein the anatomy of the patient is a pelvis.

4. The system of claim 1 wherein the surgery is a Total Hip Arthroplasty.

5. The system of claim 1 wherein the intra-operative computing unit is further configured to calculate in real-time a difference in the optical measurements in at least one degree of freedom provided by the optical sensor with respect to the registration coordinate frame and to provide the difference for display by a display unit.

6. The system of claim 1 wherein the intra-operative computing unit constructs the registration coordinate frame using redundant measurement information wherein the redundant measurement information is used to compute a metric representing the consistency between the inclination measurements and optical measurements, and the intra-operative computing unit is further configured to provide the metric to a display unit for displaying to a surgeon.

7. The system of claim 1 wherein the sensor is configured to generate optical measurements and inclination measurements relative to a common frame of reference.

8. The system of claim 7 wherein the intra-operative computing unit is configured to construct the common frame of reference using a rigid mechanical relationship between the optical sensor and the inclinometer.

9. A system comprising:
a sensor configured to attach to an anatomy of a patient comprising an optical sensor to generate optical measurements and an inclinometer configured to generate inclination measurements;
a target configured to provide positional information to the optical sensor, the optical sensor generating the optical measurements using the positional information in up to six degrees of freedom;
a probe attached to the target, the probe having a tip, wherein the tip is in a known positional relationship with the target; and
an intra-operative computing unit in communication with the sensor, the intra-operative computing unit configured to:
determine a location of two or more anatomical features of the patient using optical measurements of the sensor and the known positional relationship between the target and the tip of the probe;
calculate a direction of at least one axis defined by the location of the two or more anatomical features;
measure a direction of gravity based on the inclination measurements; and
construct a registration coordinate frame to register during surgery the anatomy of the patient based on the direction of gravity and the direction of the axis.

10. The system of claim 9 wherein the probe is removably attached to the target.

11. The system of claim 9 wherein the anatomy of the patient is a pelvis.

12. The system of claim 9 wherein the surgery is a Total Hip Arthroplasty.

13. The system of claim 11 wherein the two anatomical features lie on the anterior pelvic plane of the patient.

14. The system of claim 11 wherein the intra-operative computing unit is further configured to generate a secondary registration coordinate frame by localizing three anatomical features on the acetabular rim of the patient.

15. The system of claim 14 wherein the system is configured to provide navigational guidance based on the registration coordinate frame and the secondary registration coordinate frame.

16. A computer-implemented method comprising:
measuring, by at least one processing unit, a direction of gravity using a sensor, the sensor comprising an optical sensor and an inclinometer, attached to an anatomy of a patient positioned in a known orientation with respect to gravity;
measuring, by at least one processing unit, a direction of an axis of a device, the device having a shape defining at least one axis using positional information in up to six degrees of freedom provided by a target to the optical sensor, and a known positional relationship between the target and the device; and
constructing, by at least one processing unit, a registration coordinate frame to register during surgery the anatomy of the patient based on the direction of gravity, the direction of the axis and the known orientation of the patient with respect to gravity.

17. The method of claim 16 wherein the patient is positioned in a second orientation and the intra-operative computing unit is further configured to provide surgical navigation based on the registration coordinate frame.

18. A system comprising:
a sensor comprising an optical sensor configured to generate optical measurements and an inclinometer configured to generate inclination measurements;
a first target attached to an anatomy of a patient configured to provide positional signals in up to six degrees of freedom to the optical sensor;
a second target configured to provide positional information in up to six degrees of freedom to the optical sensor and configured to be attached to a device with a shape that defines at least one axis, wherein the at least one axis has a known positional relationship with the second target; and
an intra-operative computing unit configured to:
receive positional signals of the first target from the optical sensor;
receive inclination measurements from the inclinometer;
calculate position and orientation of the first target;
calculate the direction of gravity with respect to the position and orientation of the first target based on the inclination measurements;
measure the direction of the at least one axis using positional information provided by the second target and the known positional relationship between the second target and the device; and
construct a registration coordinate frame for the anatomy of the patient based on the direction of gravity with respect to the first target, position and orientation of the first target and the direction of axis.

19. The system of claim 18 wherein the sensor is configured to attach to an operating table.

20. The system of claim 18 wherein the sensor is configured to be held in the hand of a surgeon.

* * * * *